United States Patent [19]

Davis et al.

[11] Patent Number: 4,504,489
[45] Date of Patent: Mar. 12, 1985

[54] USE OF CERTAIN VINYL-TIN COMPOUNDS AS INSECTICIDES

[75] Inventors: Royston H. Davis, Sittingbourne, England; Mark E. Schroeder, Modesto, Calif.; Terence N. Mitchell, Dortmund 76, Fed. Rep. of Germany

[73] Assignee: Shell Oil Company, Houston, Tex.

[21] Appl. No.: 453,549

[22] Filed: Dec. 27, 1982

[30] Foreign Application Priority Data

Dec. 31, 1981 [GB] United Kingdom ............... 8139159

[51] Int. Cl.$^3$ ............................................. A01N 55/04
[52] U.S. Cl. .................................................... 514/493
[58] Field of Search ......................................... 424/288

[56] References Cited

U.S. PATENT DOCUMENTS 4,233,231 11/1980 Floyd, Jr. et al. ................. 549/209

FOREIGN PATENT DOCUMENTS 2113224 8/1983 United Kingdom ............... 424/288

Primary Examiner—Allen J. Robinson

[57] ABSTRACT

Invertebrate insects are controlled by vinyl-tin compounds in which one or both of the carbon atoms of the vinyl moiety is substituted by an oxymethyl or thiomethyl moiety.

4 Claims, No Drawings

USE OF CERTAIN VINYL-TIN COMPOUNDS AS INSECTICIDES

DESCRIPTION OF THE INVENTION

It has been found that useful insecticidal properties are possessed by vinyl-tin compounds of the formula:

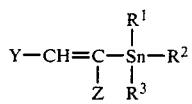  (I)

wherein each of $R^1$, $R^2$ and $R^3$ independently is alkyl; one of Y and Z is hydrogen, or alkyl, and the other of Y and Z represents a group of Formula II:

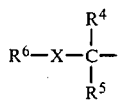  (II)

in which each of $R^4$ and $R^5$ independently is hydrogen, alkyl or alkoxy or $R^4$ and $R^5$ together with the interjacent atom represent a cycloalkyl ring; $R^6$ is hydrogen, alkyl, or alkylcarbonyl.

This invention thus provides a method of combating insects at a locus, which comprises treating the locus with a compound of Formula I, and insecticidal compositions adopted for practicing that method, said compositions comprising a insecticidal amount of an inert carrier and a compound of Formula I.

The composition and method according to the invention may if desired utilise a mixture of two or more different compounds of Formula I. If Y is other than a hydrogen atom, and Y and Z are different the compounds of Formula I exist in the form of geometric isomers. Other possibilities for isomerism may arise depending on the specific groups present in the molecule. The method of this invention embraces the use of all of the active isomers and mixtures thereof.

Unless otherwise stated, throughout this specification and claims, any alkyl moiety preferably has from 1 to 8, especially 1 to 6, carbon atoms, and a cycloalkyl group preferably has from 3 to 8 atoms in the ring.

Preferably each of $R^1$, $R^2$ and $R^3$ independently represents an unsubstituted alkyl group, especially an alkyl group having up to 8 carbon atoms. Preferably at least one, most preferably all three, of $R^1$, $R^2$ and $R^3$ represents a methyl group.

Preferably one of Y and Z represents a hydrogen atom or an unsubstituted alkyl group having 1 to 4 carbon atoms, for example a methyl group. The other represents a group of Formula II. Most preferably one of Y and Z represents a hydrogen atom and the other represents a group of Formula II.

In Formula II, if $R^4$ and $R^5$ together with the interjacent atom represent a cycloalkyl ring, this preferably has up to 8 atoms in the ring. Preferred cycloalkyl rings include cyclopentyl, cyclohexyl, cycloheptyl and cyclooctyl rings optionally substituted by one or two alkyl groups.

Preferably $R^6$ represents a hydrogen atom, an unsubstituted alkyl group having up to 4 carbon atoms, an alkylcarbonyl group having up to 4 carbon atoms in the alkyl group, or a benzoyl group. Especially preferred are compounds in which $R^6$ represents a hydrogen atom or a methyl or ethyl group.

Preferably $R^7$ represents an unsubstituted alkyl group having up to 4 carbon atoms.

Compounds of Formula I can be prepared by reacting an acetylene derivative of the formula

  (III)

with a triorgano tin hydride of the general formula

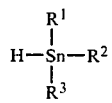  (IV)

in which $R^1$, $R^2$, $R^3$, Y and Z have the meanings given for the novel compounds above.

In general, this process leads to a mixture of different compounds of the Formula I since the $-SnR^1R^2R^3$ group can add to either carbon atom of the acetylenic bond. In addition, mixtures of geometric isomers are generally produced. The exact ratio of products produced depends of course on the precise reaction condition. The reaction products may be separated into individual components by conventional means.

The molar ratio of the reactants is not critical, and may for example be in the range of from 5:1 to 1:5, especially 2:1 to 1:2. It may be convenient to use an approximately stoichiometric ratio of reactants.

The reaction is preferably carried out at a temperature in the range of from 0° to 150° C., especially 40° to 110° C. The reaction may conveniently be carried out under reflux.

If one or both of the reactants is a liquid, it may be convenient to carry out the reaction without the addition of a separate solvent. Generally however it is preferred that a suitable inert solvent be present. Suitable solvents include, for example, hydrocarbons, for example toluene, ethers, for example diethyl ether, and esters, for example ethyl acetate.

The reaction is a free radical reaction, and is therefore preferably initiated in one of the ways normally used for radical reactions, for example using a small amount of a compound which itself produces free radicals, such as an azo compound or a peroxide. Photo-initiation may be used, and for some reactions thermal initiation is adequate.

The compounds of the general formula I are active against a range of insect and acarid pests and, surprisingly, against the eggs of certain pests. Many pesticides suffer the disadvantage that they are not effective against pests in all stages of their development, either because they lack the necessary spectrum of activity, or because they are difficult to apply to eggs directly, since eggs tend to be laid in inaccessible places, such as the underside of leaves. In general, the compounds of the general formula I have a wide spectrum of activity and, in addition, many are relatively volatile liquids which are active in the vapour phase. This enables them to combat eggs laid in places inaccessible to normal pesticide sprays.

A composition according to the invention comprises one or more carriers. A carrier is any material with which the active ingredients are formulated to facilitate application to the locus to be treated, or to facilitate storage, transport or handling. A carrier may be a solid or a liquid, including a material which is normally gaseous but which has been compressed to form a liquid, and any of the carriers normally used in formulating pesticidal compositions may be used.

Suitable solid carriers include natural and synthetic clays and silicates, for example natural silicas such as diatomaceous earths; magnesium silicates, for example talcs; magnesium aluminium silicates, for example attapulgites and vermiculites; aluminium silicates, for example kaolinites, montmorillonites and micas; calcium carbonate; calcium sulphate; synthetic hydrated silicon oxides and synthetic calcium or aluminium silicates; elements, for example carbon and sulphur; natural and synthetic resins, for example coumarone resins, polyvinyl chloride, and styrene polymers and copolymers; solid polychlorophenols; bitumen; waxes, for example beeswax, paraffin wax, and chlorinated mineral waxes; and solid fertilisers, for example superphosphates.

Suitable liquid carriers include water; alcohols, for example isopropanol and glycols; for example acetone, methyl ethyl ketone, methyl isobutyl ketone and cyclohexanone; ethers; aromatic or araliphatic hydrocarbons, for example benzene, toluene and xylene; petroleum fractions, for example kerosine and light mineral oils; chlorinated hydrocarbons, for example carbon tetrachloride, perchloroethylene and trichloroethane. Mixtures of different liquids are often suitable.

Agricultural compositions are often formulated and transported in a concentrated form which is subsequently diluted by the user before application. The presence of small amounts of a carrier which is a surface-active agent facilitates this process of dilution.

A surface-active agent may be an emulsifying agent, a dispersing agent or a wetting agent; it may be nonionic or ionic. Examples of suitable surface-active agents include the sodium or calcium salts of polyacrylic acids and lignin sulphonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohol or alkyl phenols, for example p-octylphenol or p-octylcresol, with ethylene oxide and/or propylene oxide; sulphates or sulphonates of these condensation products; alkali or alkaline earth metal salts, preferably sodium salts, of sulphuric or sulphonic acid esters containing at least 10 carbon atoms in the molecule, for example sodium lauryl sulphate, sodium secondary alkyl sulphates, sodium salts of sulphonated castor oil, and sodium alkylaryl sulphonates such as sodium dodecylbenzene sulphonate; and polymers of ethylene oxide and copolymers of ethylene oxide and propylene oxide.

The compositions of the invention may for example be formulated as wettable powders, dusts, granules, solutions, emulsifiable concentrates, emulsions, suspension concentrates and aerosols. Wettable powders usually contain 25, 50 and 75% w of active ingredient and usually contain, in addition to solid inert carrier, 3–10% w of a dispersing agent and, where necessary, 0–10% w of stabiliser(s) and/or other additives such as penetrants or stickers. Dusts are usually formulated as a dust concentrate having a similar compositions to that of a wettable powder but without a dispersant, and are diluted in the field with further solid carrier to give a composition usually containing ½–10% w of active ingredient.

Granules are usually prepared to have a size between 10 and 100 BS mesh (1.676–0.152 mm), and may be manufactured by agglomeration or impregnation techniques. Generally, granules will contain ½–25% w active ingredient and 0–10% w of additives such as stabilisers, slow release modifiers and binding agents. Emulsifiable concentrates usually contain, in addition to a solvent and, when necessary co-solvent, 10–50% w/v active ingredient, 2–20% w/v emulsifiers and 0–20% w/v of other additives such as stabilisers, penetrants and corrosion inhibitors. Suspension concentrates are usually compounded so as to obtain a stable, non-sedimenting flowable product and usually contain 10–75% w active ingredient, 0.5–15% w of dispersing agents, 0.1–10% w of suspending agents such as protective colloids and thixotropic agents, 0–10% w of other additives such as defoamers, corrosion inhibitors, stabilisers, penetrants and stickers, and water or an organic liquid in which the active ingredient is substantially insoluble; certain organic solids or inorganic salts may be present dissolved in the formulation to assist in preventing sedimention or as anti-freeze agents for water.

Aqueous dispersions and emulsions, for example compositions obtained by diluting a wettable powder or a concentrate according to the invention with water, also lie within the scope of the present invention. The said emulsions may be of the water-in-oil or of the oil-in-water type, and may have a thick 'mayonnaise'-like consistency.

The compositions of the invention may also contain other ingredients, for example, other compounds possessing pesticidal, herbicidal or fungicidal properties.

The following examples show preparation of individual species of the compounds of Formula I. In each case, the indentity of the product, and of any intermediate involved, was confirmed by appropriate chemical and spectral analyses.

EXAMPLE 1

Preparation of:

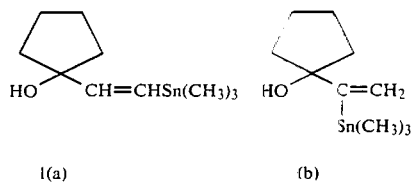

1(a)  (b)

A mixture of trimethyltin hydride (3.2 g) and 1-ethynylcyclopentanol (2.2 g) was stirred vigorously and heated slowly to a temperature between 65° and 75° C. The mixture was then refluxed for about three quarters of an hour. After this time, the reaction mixture was worked-up by chromatography over alumina Using hexane and diethyl ether as eluants. The three main fractions obtained were shown by NMR to be the cis isomer of compound 1(a); the trans isomer of compound 1(a) and compound 1(b).

| Analysis: | | Physical Data: |
|---|---|---|
| Calculated C:H content | C: 43.6 H: 7.4 | $n_D^{18} = 1.5110$ |
| Found for cis isomer of 1(a) | C: 43.5 H: 7.4 | |
| Found for trans isomer of 1(a) | C: 43.5 H: 8.0 | $n_D^{18} = 1.5150$ |

| Analysis: | Physical Data: |
|---|---|
| Found for compound 1(b) | C: 43.4  H: 8.0  $n_D^{18.5} = 1.5138$ |

EXAMPLES 2 to 27

By methods analogous to that described in Example 1, the following compounds of the general formula I were prepared. In all cases, the initial product consisted of a mixture of isomers denoted by * in Table 1. In some cases, the mixture was separated into individual isomers, denoted by (a)t, (a)c, and (b) as defined below:

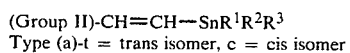

Type (a)-t = trans isomer, c = cis isomer

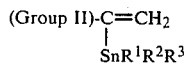

Type (b)

Analysis and physical data figures are given in Table 1 where available.

TABLE 1

| Example No. | $R^1$ | $R^2$ | $R^3$ | Group II | Analysis | | | Physical Data |
|---|---|---|---|---|---|---|---|---|
| 2 (a)c | CH$_3$ | CH$_3$ | CH$_3$ | 1-hydroxycycloheptyl | Calculated: Found: | C: 47.6  H: 8.0 C: 47.6  H: 8.0 | | $n_D^{18.5}$ 1.5150 |
| 2 (a)t | | | | | Found: | C: 47.6  H: 8.2 | | $n_D^{18.5}$ 1.5195 |
| 2 (b) | | | | | Found: | C: 47.5  H: 8.4 | | $n_D^{19.0}$ 1.5185 |
| Example No. | $R_1$ | $R_2$ | $R_3$ | Group II | Analysis | | | Physical Data |
| 3 (a)t | CH$_3$ | CH$_3$ | CH$_3$ | 1-acetoxy-cyclohexyl | Calculated Found: | C: 47.3  H: 7.3 C: 47.1  H: 7.4 | | $n_D^{20.8} = 1.486$ |
| 3 (a)c | | | | | Found: | C: 47.8  H: 7.5 | | $n_D^{20.8} = 1.498$ |
| 4 (a)t | CH$_3$ | CH$_3$ | CH$_3$ | α-hydroxy-benzyl | Calculated: Found: | C: 48.5  H: 6.1 C: 49.0  H: 6.3 | | $n_D^{23} = 1.5500$ |
| 4 (b) | | | | | Found: | C: 48.3  H: 6.3 | | $n_D^{23} = 1.5506$ |
| 5 (a)c | CH$_3$ | CH$_3$ | CH$_3$ | 1-methoxy-cyclohexyl | Calculated: Found: | C: 47.6  H: 8.0 C: 47.5  H: 8.1 | | $n_D^{23} = 1.4953$ |
| 5 (a)t | | | | | Found: | C: 47.6  H: 8.3 | | $n_D^{22} = 1.4960$ |
| 5 (b) | | | | | Found: | C: 47.4  H: 8.1 | | $n_D^{23} = 1.4955$ |
| 6 (a)c | CH$_3$ | CH$_3$ | CH$_3$ | α-hydroxy(3-phenoxybenzyl) | Calculated: Found: | C: 55.6  H: 5.7 C: 55.6  H: 5.9 | | $n_D^{23} = 1.5778$ |
| 6 (a)t | | | | | Found: | C: 55.4  H: 6.0 | | $n_D^{23} = 1.5795$ |
| 6 (b) | | | | | Found: | C: 55.8  H: 5.8 | | $n_D^{23} = 1.5772$ |
| 7 (a)c | CH$_3$ | CH$_3$ | CH$_3$ | 1-hydroxy-2-methylcyclo-hexyl | Calculated: Found: | C: 47.8  H: 7.6 C: 48.0  H: 7.8 | | |
| 7 (a)t | | | | | Found: | C: 47.8  H: 8.0 | | |
| 8 (a)c | CH$_3$ | CH$_3$ | CH$_3$ | 1-hydroxy-cyclooctyl | Calculated: Found: | C: 49.3  H: 8.3 C: 49.2  H: 8.3 | | $n_D^{23} = 1.5150$ |
| 8 (a)t | | | | | Found: | C: 49.6  H: 8.4 | | $n_D^{18.5} = 1.5195$ |
| 8 (b) | | | | | Found: | C: 49.6  H: 8.7 | | $n_D^{19} = 1.5185$ |
| 9* | CH$_3$ | CH$_3$ | CH$_3$ | 2-hydroxy-6-methylhept-2-yl | | | | |
| 10 (a)c | CH$_3$ | CH$_3$ | CH$_3$ | 2,4-dimethyl-3-hydroxypent-3-yl | Calculated: | C: 47.2  H: 8.6 | | |
| 10 (a)t 10 | | | | | Found: | C: 47.3  H: 9.1 | | Oil |
| 11* | CH$_3$ | CH$_3$ | CH$_3$ | 1-hydroxy-4-t-butylcyclo-hexyl | Calculated: Found: | C: 52.2  H: 8.7 C: 52.6  H: 9.2 | | Mpt 83–85° C. |
| 12* | CH$_3$ | CH$_3$ | CH$_3$ | 1,2-dihydroxy-cyclohexyl | Calculated: Found: | C: 43.3  H: 7.3 C: 43.9  H: 7.9 | | bpt 130° C. at 0.045 mm pressure. |
| 13* | CH$_3$ | CH$_3$ | CH$_3$ | 2-hydroxypent-2-yl | | | | |
| 14* | CH$_3$ | CH$_3$ | CH$_3$ | Ethoxymethyl | | | | |
| 15 (a)t | CH$_3$ | CH$_3$ | C$_2$H$_5$ | 1-hydroxy-cyclohexyl | Calculated: Found: | C: 47.6  H: 7.9 C: 47.1  H: 8.0 | | $n_D^{23} = 1.5155$ |
| 15 (a)c plus 15 (b) | | | | | Found: | C: 47.9  H: 7.9 | | |
| 16* | CH$_3$ | n-C$_4$H$_9$ | n-C$_4$H$_9$ | 1-hydroxy-cyclohexyl | Calculated: Found: | C: 54.7  H: 9.2 C: 55.1  H: 9.5 | | bpt 160° C. at 0.1 mm pressure |
| 17* | n-C$_4$H$_9$ | n-C$_4$H$_9$ | n-C$_4$H$_9$ | 1-hydroxy-cyclohexyl | | | | |
| 18* | n-C$_4$H$_9$ | n-C$_4$H$_9$ | n-C$_4$H$_9$ | 2-hydroxybut- | | | | |

TABLE 1-continued

| | | | | | | | | |
|---|---|---|---|---|---|---|---|---|
| 19* | n-C$_4$H$_9$ | n-C$_4$H$_9$ | n-C$_4$H$_9$ | 2-yl 2-hydroxyprop-2-yl | | | | |
| 20 (a)c | CH$_3$ | CH$_3$ | CH$_3$ | 1-hydroxy-cyclohexyl | Calculated: Found: | C: 45.7 C: 45.2 | H: 7.7 H: 7.7 | $n_D^{18.5} = 1.5080$ |
| 20 (a)t | | | | | Found: | C: 45.2 | H: 7.7 | mpt 50° C. |
| 20 (b) | | | | | Found: | C: 46.4 | H: 8.2 | $n_D^{18.5} = 1.5088$ |
| 20* | | | | | | | | Bpt = 70–73° C. at 0.02 mm pressure |
| 21* | CH$_3$ | CH$_3$ | CH$_3$ | 2-hydroxy-prop-2-yl | | | | |
| 22* | CH$_3$ | CH$_3$ | CH$_3$ | 2-hydroxybut-2-yl | | | | |
| 23* | n-C$_4$H$_9$ | n-C$_4$H$_9$ | n-C$_4$H$_9$ | 2-hydroxy-6-methylhept-2-yl | | | | |
| 24* | CH$_3$ | CH$_3$ | CH$_3$ | diethoxymethyl | Calculated: Found: | C: 40.9 C: 40.0 | H: 7.6 H: 7.9 | bpt 70–75° C. at at 0.7 mm pressure |
| 25* | CH$_3$ | CH$_3$ | n-C$_5$H$_{11}$ | 1-hydroxy-cyclohexyl | Calculated: Found: | C: 52.2 C: 52.3 | H: 8.8 H: 8.7 | |
| 26 (a)c | CH$_3$ | CH$_3$ | n-C$_4$H$_9$ | 1-hydroxy-cyclohexyl | Calculated: Found: | C: 47.6 C: 46.5 | H: 7.9 H: 8.3 | |
| 26 (a)t | | | | | Found: | C: 47.1 | H: 8.2 | $n_D^{23} = 1.5155$ |
| 27* | CH$_3$ | CH$_3$ | CH$_3$ | Methoxymethyl | | | | |

EXAMPLES 28 and 29

By methods analogous to that described in Example 1, the following compounds were prepared.

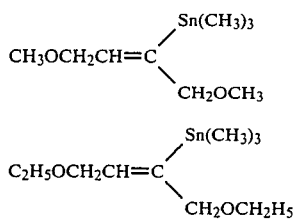

$$CH_3OCH_2CH=C\begin{matrix}Sn(CH_3)_3\\ \\CH_2OCH_3\end{matrix} \quad 28$$

$$C_2H_5OCH_2CH=C\begin{matrix}Sn(CH_3)_3\\ \\CH_2OCH_2H_5\end{matrix} \quad 29$$

EXAMPLE 30

The insecticidal, acaricidal and ovicidal activities of the compounds of the invention were assessed employing the following pests.

| Insect: | Spodoptera littoralis | (S.l.) |
|---|---|---|
| | Aedes aegypti | (a.a) |
| | Musca domestica | (m.d.) |
| | Aphid fabae | (a.f.) |
| Acarids: | Tetranychus urticae | (T.u.) |
| Eggs of: | Tetranychus urticae | (ovicide - T.u.) |
| | Spodoptera Littoralis | (ovicide - S.l.) |

The test methods employed for each species appear below; in each test, unless otherwise stated, a 0.2% solution or suspension of each test compound in 16.7% acetone in water containing 0.04% Triton X-100 (Trade Mark) was sprayed onto the test species; controls were sprayed with a control solution of water, acetone and Triton X-100 (Trade Mark) in the same proportions. The tests were all conducted under normal insectary conditions 23° C.±2° C. (fluctuating light and humidity.

(i) *Spodoptera littoralis*

Second instar larvae were used in the tests. Each test solution and the control solution was sprayed onto a separate petri dish containing a nutrious diet on which the *Spodoptera littoralis* larvae had been reared.

When the spray deposit had dried each dish was infested with 10 2nd instar larvae. Mortality assessments were made 1 and 7 days after spraying and the percentage mortality calculated.

(ii) *Aedes aegypti*

Early 4th instar larvae were used in the tests. Test solutions were made up to 3 ppm of active ingredient in water containing 0.04% Triton×100 (Trade Mark); acetone was initially present to aid solution, but was subsequently allowed to evaporate off.

Ten early 4th instar larvae were placed in 100 ml of the test solution. After 48 hours, larval mortality (as a percentage) was recorded.

Any surviving larvae were then fed with a small quantity of animal feed pellets and the final percentage mortality of adults and pupae made when all the larvae has either pupated and turned into adults, or died.

(iii) *Musca domestica*

Female adult flies (2–3 days old) were used for the tests. Batches of ten flies anaesthetised with carbon dioxide on filter paper were placed inside 9 cm plastic petri dishes. The anaesthetised flies were sprayed with the test solutions and control solution and half an hour after spraying 300 μl of milk were pipetted onto the filter paper inside the petri dishes. After 24 hours the number of dead and moribund flies was assessed and the percentage mortality calculated.

(iv) *Aphis fabae*

Adult aphids (5–7 days old) were used in the tests. Pairs of leaves were removed from broad bean plants and these were placed ventral side uppermost on filter paper inside 9 cm plastic petri dishes. Groups of ten to twenty aphids were transferred onto filter paper inside 5 cm petri dishes where they were then covered with wire mesh lids. The two types of petri dishes containing leaves and aphids were then sprayed in parallel and the leaves left for ½–1 hour to dry; when dry each pair of leaves was infested with the corresponding group of sprayed aphids. The number of dead and moribund insects on each pair of leaves was assessed after 24 hours and the percentage mortality calculated.

(v) *Tetranychus urticae*

Adult mites were used in the tests. Disks of diameter 2 cm were cut from the leaves of French bean plants and were placed on filter paper kept moist by a cotton wool wick dipping into water in a plastic carton. Prior to testing, each leaf disk was infested with ten mites; the mites and disk were then sprayed, each with one test solution.

The dead and moribund individuals were assessed After 48 hours and the percentage mortality calculated.

(iv) *Tetranychus urticae* ovicide.

Eggs less than 24 hours old were used for testing.

Disks of diameter 2 cm were cut from the leaves of French bean plants and were placed on filter paper kept moist by a cotton wool wick dipping into water in a plastic carton. On the day before spraying each leaf disk was infested with 10 adult mites. On the day of the test before spraying the adult mites were removed from the leaf disks leaving the eggs laid overnight by the mites on the disks.

Seven to ten days after spraying the numbers of hatched nymphs and unhatched eggs were assessed and the percentage mortality calculated.

(vii) *Spodoptera littoralis* ovicide

Eggs less than 24 hours old were used in the tests

Adult *Spodoptera littoralis* were held in large plastic cylinders containing blotting paper on which the moths laid their batchs of eggs. Egg batches containing approximately 60-70 eggs were cut from the blotting paper with a 1 cm surround. These were placed eggs uppermost on filter paper in the deeper half of 5 cm disposable petri dishes and each batch of eggs was then sprayed with a different test solution or the control solution. The dishes were covered until the control eggs had hatched, approximately 5 days. The percentage ovicidal mortality was then calculated.

The results of these tests are shown in Table 2 in which the test species are identified by the initials noted above and the activity of each compound is expressed in terms of the percentage mortality:

A denotes 90–100% mortality
B denotes 50–80% mortality
C denotes 0–40% mortality A blank space in Table 2 indicates that the compound was not tested, usually because there was an insufficient quantity of the compound available for testing in all the tests.

The compounds tested are identified in the same way as in Table 1.

TABLE 2

| Compound No. | Sl 24 h | Sl 7 day | Aa 48 h | Aa Final | Md 24 h | Af 24 h | Tu 48 h | ovicide Tu | ovicide Sl |
|---|---|---|---|---|---|---|---|---|---|
| 1(a)c | | | | | | | | | A |
| 1(a)t | A | A | A | A | A | A | A | A | A |
| 1(b) | | | | | | | | | A |
| 2(a)c | | | | | | | | | A |
| 2(a)t | A | A | A | A | A | A | A | A | A |
| 2(b) | | | | | | | | | A |
| 3(a)c | | | | | | | | | A |
| 3(a)t | A | A | A | A | A | A | A | B | A |
| 4(a)c | A | A | A | A | A | A | A | A | A |
| 4(a)t | A | A | A | A | A | A | A | A | A |
| 5(a)c | A | A | A | A | A | A | A | A | A |
| 5(a)t | A | A | A | A | A | A | A | A | A |
| 5(b) | A | A | A | A | A | A | A | A | A |
| 6(a)c | A | A | A | A | A | A | A | A | A |
| 6(a)t | A | A | A | A | A | A | A | A | A |
| 6(b) | A | A | A | A | A | A | A | A | A |
| 7(a)c | A | A | A | A | A | A | A | A | A |
| 7(a)t | A | A | A | A | A | A | A | A | A |
| 8(a)c | A | A | A | A | A | A | A | A | A |
| 8(a)t | A | A | A | A | A | A | A | A | A |
| 8(b) | A | A | A | A | A | A | A | A | A |
| 9* | A | A | A | A | A | A | A | A | A |
| 10(a)c | A | A | | | | | | | A |
| 10(a)t | A | A | | | | | | | A |
| 11* | A | A | A | A | A | A | A | A | A |
| 13* | A | A | A | A | A | A | B | A | A |
| 14* | C | C | C | A | A | A | C | C | A |
| 15(a)c | A | A | A | A | A | A | A | A | A |
| 16* | | A | | | | | | | A |
| 17* | C | A | C | A | C | A | A | A | C |
| 18* | C | B | C | A | C | C | A | B | C |
| 19* | C | B | C | A | C | B | A | A | C |
| 20(a)c | | | | | | | | | A |
| 20(a)t | A | A | A | A | A | A | A | A | A |
| 20(b) | | | | | | | | | A |
| 20* | A | A | A | A | A | A | A | A | A |
| 21* | A | A | B | A | A | A | C | C | A |
| 22* | A | A | B | A | A | A | C | C | A |
| 23* | C | B | C | A | C | C | A | A | C |
| 27* | C | B | C | A | A | C | C | A | C |
| 28* | C | A | B | A | A | A | C | B | A |
| 29* | B | A | C | A | A | A | A | B | A |

We claim:

1. An insecticidal composition which comprises an agricultural carrier, a surface-active agent, and an insecticidal amount of a compound of the formula:

wherein each of $R^1$, $R^2$ and $R^3$ independently is alkyl of one to eight carbon atoms; one of Y and Z is hydrogen, or alkyl of one to four carbon atoms, and the other is a group of Formula II:

in which each of $R^4$ and $R^5$ independently is hydrogen, or alkyl or alkoxy of one to eight carbon atoms, or $R^4$ and $R^5$ together with the interjacent carbon atom form a cycloalkyl ring of from five to eight carbon atoms; $R^6$ is hydrogen, alkyl of from one to four carbon atoms, alkylcarbonyl having up to four carbon atoms in the alkyl group or benzoyl.

2. A composition according to claim 1 wherein each of $R^1$, $R^2$ and $R^3$ is methyl, Z is hydrogen, $R^6$ is hydrogen and $R^4$ and $R^5$ together with the linking carbon atom form a cyclohexyl ring.

3. A method of combating insects at a locus which comprises treating the locus with an insecticidal amount of a compound of claim 1.

4. A method according to claim 3 wherein each of $R^1$, $R^2$ and $R^3$ is methyl, Z is hydrogen, $R^6$ is hydrogen and $R^4$ and $R^5$ together with the linking carbon atom form a cyclohexyl ring.

* * * * *